US008834494B2

(12) United States Patent
Schorr et al.

(10) Patent No.: US 8,834,494 B2
(45) Date of Patent: Sep. 16, 2014

(54) METHOD AND DEVICE FOR AUTOMATED NEEDLE DEPLOYMENT

(75) Inventors: Gary James Schorr, Apple Valley, MN (US); Jyue Boon Lim, New Brighton, MN (US)

(73) Assignee: St. Jude Medical, Cardiology Division, Inc., Minnetonka, MN (US)

( * ) Notice: Subject to any disclaimer, the term of this patent is extended or adjusted under 35 U.S.C. 154(b) by 1266 days.

(21) Appl. No.: 11/551,620

(22) Filed: Oct. 20, 2006

(65) Prior Publication Data

US 2008/0097481 A1 Apr. 24, 2008

(51) Int. Cl.
| | |
|---|---|
| A61B 17/04 | (2006.01) |
| A61B 17/062 | (2006.01) |
| A61B 17/29 | (2006.01) |
| A61B 17/06 | (2006.01) |

(52) U.S. Cl.
CPC ..... *A61B 17/0469* (2013.01); *A61B 2017/2912* (2013.01); *A61B 17/06123* (2013.01); *A61B 17/0625* (2013.01); *A61B 2017/047* (2013.01); *A61B 2017/06095* (2013.01); *A61B 2017/0472* (2013.01)
USPC .......................... 606/144; 606/139; 606/148

(58) Field of Classification Search
USPC .................................. 606/144, 148, 145–147
See application file for complete search history.

(56) References Cited

U.S. PATENT DOCUMENTS

| | | | |
|---|---|---|---|
| 5,084,058 A | 1/1992 | Li | |
| 5,324,298 A | 6/1994 | Phillips et al. | |
| 5,364,408 A | 11/1994 | Gordon | |
| 5,458,609 A * | 10/1995 | Gordon et al. | 606/144 |
| 5,496,348 A | 3/1996 | Bonnuti | |
| 5,562,684 A | 10/1996 | Kammerer | |
| 5,578,044 A | 11/1996 | Gordon et al. | |
| 5,643,292 A | 7/1997 | Hart | |
| 5,797,928 A | 8/1998 | Kogasaka | |
| 5,845,645 A | 12/1998 | Bonutti | |
| 5,868,762 A * | 2/1999 | Cragg et al. | 606/144 |
| 5,984,933 A | 11/1999 | Yoon | |
| 5,993,459 A | 11/1999 | Larsen et al. | |
| 6,059,800 A | 5/2000 | Hart et al. | |
| 6,074,395 A | 6/2000 | Trott et al. | |
| 6,077,276 A | 6/2000 | Kontos | |
| 6,132,439 A | 10/2000 | Kontos | |

(Continued)

FOREIGN PATENT DOCUMENTS

WO          9627331 A1     9/1996

OTHER PUBLICATIONS

International Search Report, PCT/US2007/022237, mailed Feb. 28, 2008.

*Primary Examiner* — Dianne Dornbusch
*Assistant Examiner* — Alexander Orkin
(74) *Attorney, Agent, or Firm* — Holland & Hart

(57) ABSTRACT

An automated needle deployment device is provided. In one embodiment, the automated needle deployment device comprises a pusher, a needle, a tube, and an actuator. The pusher has a needle engaging end. The needle has a sharp end and an opposite end. A suture is associated with the needle. The pusher and needle are slidably disposed within the tube. The actuator comprises a control and a spring and is operatively associated with the pusher. Actuation of the actuator moves the pusher towards the needle expulsion end of the tube such that the needle engaging end of the pusher engages the needle and expels the needle from the tube.

16 Claims, 13 Drawing Sheets

(56) References Cited

U.S. PATENT DOCUMENTS

| | | | |
|---|---|---|---|
| 6,136,010 A * | 10/2000 | Modesitt et al. | 606/144 |
| 6,283,947 B1 | 9/2001 | Mirzaee | |
| 6,358,258 B1 * | 3/2002 | Arcia et al. | 606/139 |
| 6,358,259 B1 | 3/2002 | Swain et al. | |
| 6,533,795 B1 * | 3/2003 | Tran et al. | 606/144 |
| 6,702,825 B2 | 3/2004 | Frazier et al. | |
| 6,716,224 B2 | 4/2004 | Singhatat | |
| 6,855,124 B1 | 2/2005 | Gonzalez et al. | |
| 7,112,207 B2 * | 9/2006 | Allen et al. | 606/139 |
| 7,160,309 B2 * | 1/2007 | Voss | 606/144 |
| 7,226,467 B2 | 6/2007 | Lucatero et al. | |
| 2003/0040712 A1 | 2/2003 | Ray et al. | |
| 2003/0181926 A1 | 9/2003 | Dana et al. | |
| 2004/0068273 A1 | 4/2004 | Fariss et al. | |
| 2004/0097973 A1 * | 5/2004 | Loshakove et al. | 606/144 |
| 2005/0033319 A1 | 2/2005 | Gambale et al. | |
| 2005/0159812 A1 | 7/2005 | Dinger et al. | |
| 2005/0182427 A1 * | 8/2005 | Manzo | 606/144 |
| 2007/0203507 A1 * | 8/2007 | McLaughlin et al. | 606/144 |
| 2007/0213757 A1 * | 9/2007 | Boraiah | 606/184 |
| 2008/0033459 A1 | 2/2008 | Shafi et al. | |
| 2008/0097479 A1 | 4/2008 | Boehlke et al. | |
| 2008/0097480 A1 | 4/2008 | Schorr et al. | |
| 2008/0097484 A1 | 4/2008 | Lim et al. | |
| 2008/0097527 A1 | 4/2008 | Lim et al. | |

\* cited by examiner

METHOD AND DEVICE FOR AUTOMATED NEEDLE DEPLOYMENT

FIELD OF THE INVENTION

The present invention generally relates to medical systems and devices for suturing internal tissue walls, and more particularly to a device for automated needle deployment and to a method of using such device.

BACKGROUND OF THE INVENTION

Various medical procedures, particularly cardiology procedures, involve accessing a corporeal vessel through the formation of a hole or opening in the vessel wall so that a medical procedure can be performed. After the particular medical procedure has been performed, the access hole in the vessel wall must be closed.

A number of prior vascular closure devices and methods have been developed in attempt to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. Nos. 5,643,292 and 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use. Furthermore, many suturing devices dilate the vessel opening and perform the medical procedure via the vessel opening before the suture is extended across the vessel opening for approximation tissue surrounding the vessel wall.

In many prior art systems, needle deployment is done manually by a physician or operator. Manual deployment involves estimation by the operator of how the needle should be deployed, how fast the trigger for the needle should be actuated, how much force should be applied, etc. The manual method of needles deployment require the physician to manually pull a lever or button proximally to deploy the needles. The speed or force used to actuate the lever or button will determine the force the needle will have when penetrating the artery. The more force the needle have in penetrating the artery the greater the possibility of piercing an artery. Thus, the physician must exert sufficient force to penetrate the artery but take care not to exert so much force as to pierce the artery. Manual deployment allows for greater inconsistency and user error as different physicians have differing perception when it comes to how much force or speed to apply when using a device It would be advantageous to have a device for automated needle deployment that reduces operator estimation and, thus, operator error, and standardizes deployment of the needle.

BRIEF SUMMARY OF THE INVENTION

A device for automated needle deployment and a method of using such device is disclosed. Medical systems and devices for suturing internal tissue walls that include such automated needle deployment device are further disclosed.

In one embodiment, the automated needle deployment device comprises a pusher, a needle, a tube, and an actuator. The pusher has a needle engaging end. The needle has a sharp end and an opposite end. A suture is associated with the needle. The pusher and needle are slidably disposed within the tube. The actuator comprises a control and a spring and is operatively associated with the pusher. Actuation of the actuator moves the pusher towards the needle expulsion end of the tube such that the needle engaging end of the pusher engages the needle and expels the needle from the tube.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

FIG. 2b illustrates an alternative view of the needle and suture of FIG. 2a.

DETAILED DESCRIPTION OF THE INVENTION

A device for automated needle deployment and a method of using such device is disclosed. Medical systems and devices for suturing internal tissue walls included such automated needle deployment device are further disclosed. More particularly, an automated needle deployment device suitable for use with an internal tissue suture delivery system for performing medical procedures that include delivering needles and sutures to internal tissue for closing internal tissue walls after an opening or puncture in tissue has been made is provided. The automated needle deployment device may form a part of a needle and suture delivery unit. Tissue that may be closed in accordance with the teachings herein may be part of a lumen such as a blood vessel, body cavity, other organ, or any tissue suitable for suturing. In one example, vascular suture delivery systems such as disclosed in copending U.S. patent application Ser. No. 11/551,523, filed Oct. 20, 2006, may be used to deliver needles and sutures for closing internal tissue walls after a medical procedure is performed through a vascular wall opening.

Figure 1A:
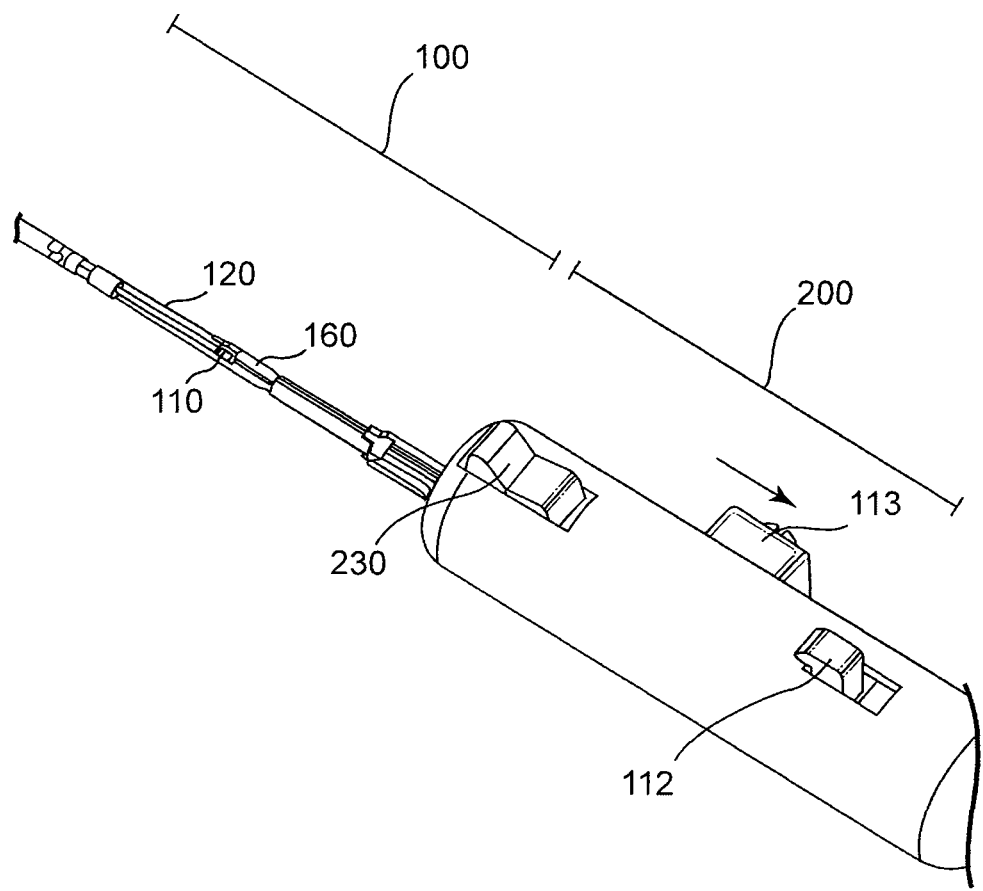
FIG. 1a illustrates an automated needle deployment device in a closed configuration in accordance with one embodiment.
Figure 1B:
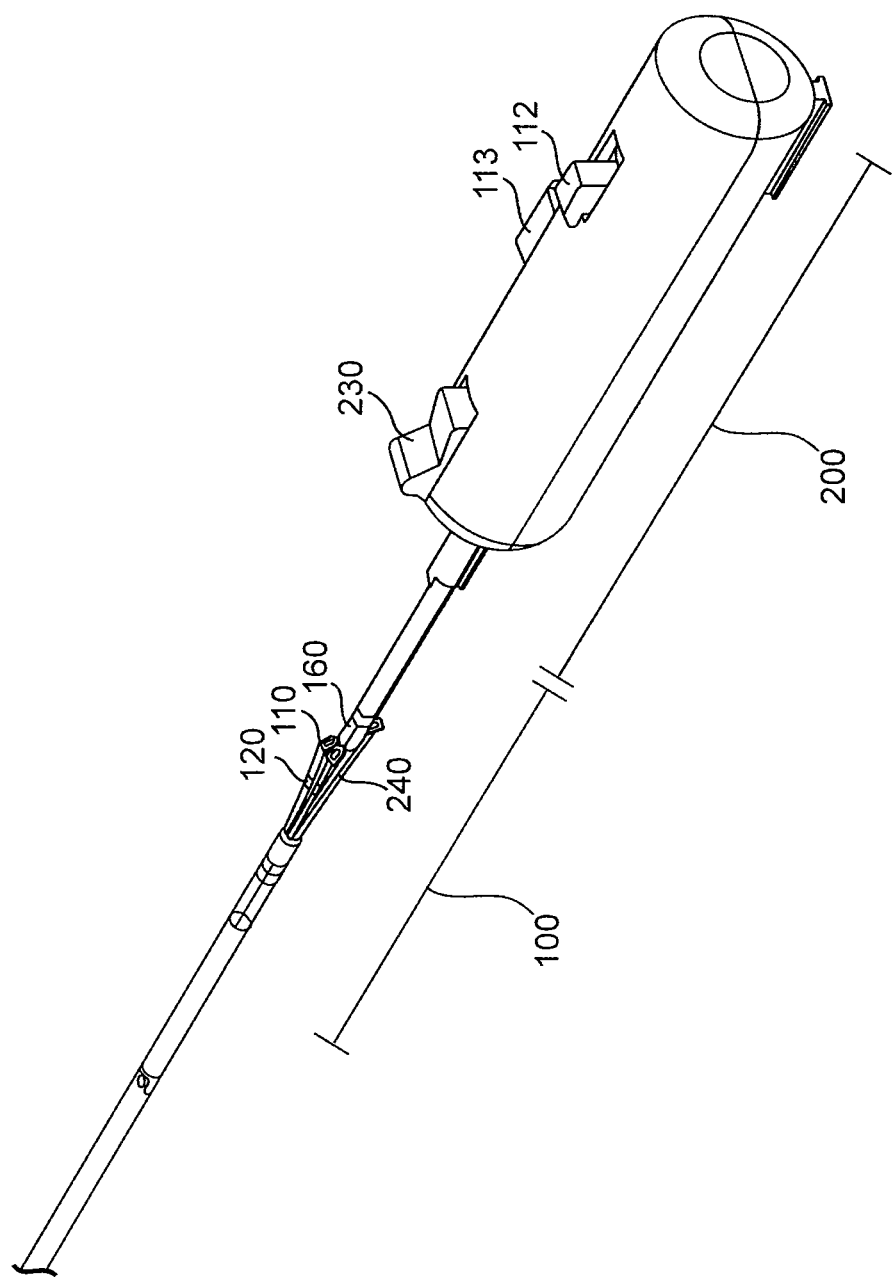
FIG. 1b illustrates an automated needle deployment device in a partially open configuration in accordance with one embodiment.
Figure 1C:
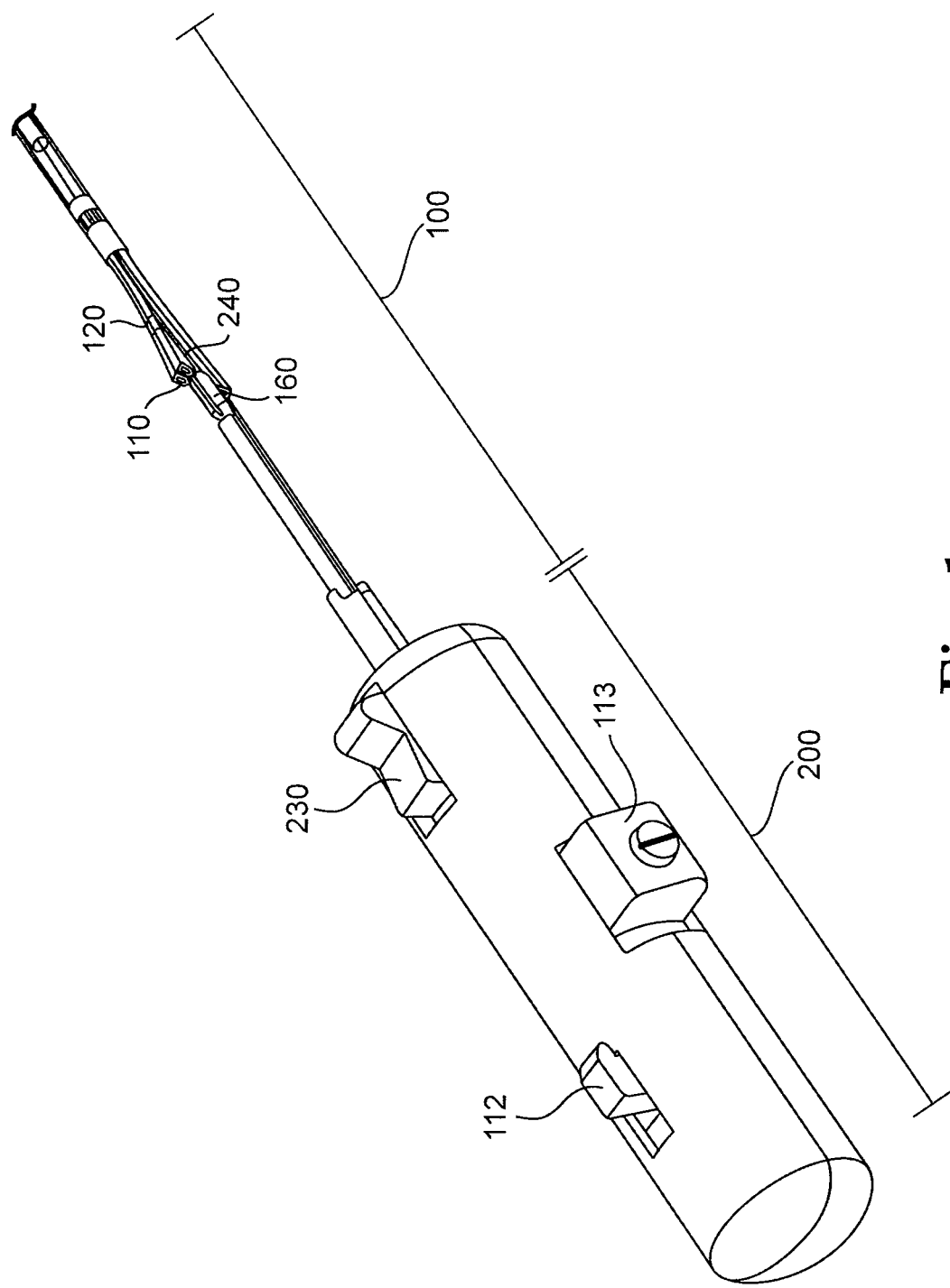
FIG. 1c illustrates an automated needle deployment device in an open configuration in accordance with one embodiment.
Figure 1D:
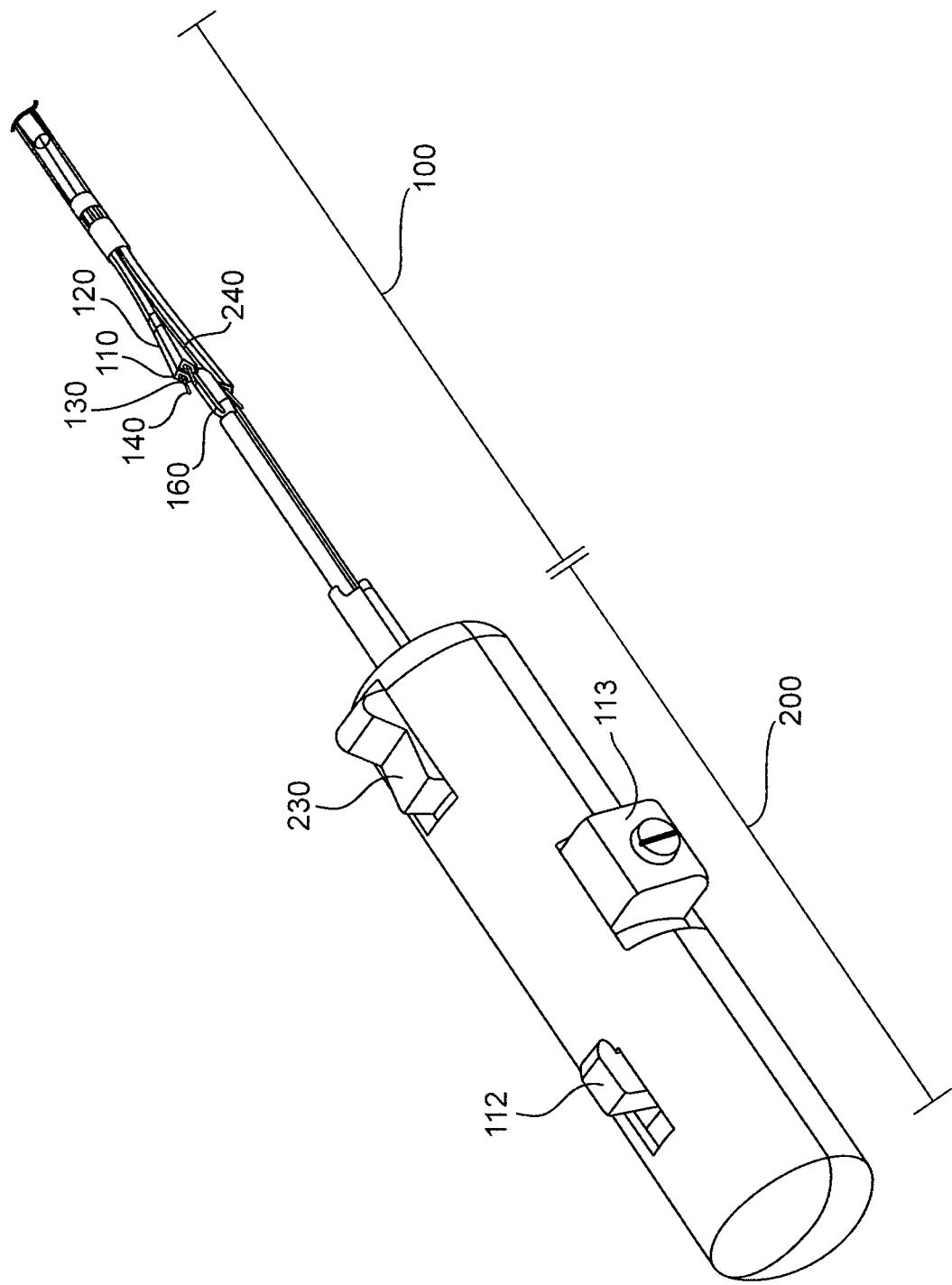
FIG. 1d illustrates an automated needle deployment device in a needle deploying configuration in accordance with one embodiment.

FIGS. 1a-1d illustrate one embodiment of a vascular closure delivery system comprising a handle and needle and suture delivery unit 100. FIG. 1a illustrates the needle and suture delivery unit in a closed configuration, FIGS. 1b and 1c illustrates the needle and suture delivery unit in a partially open and an open configuration, respectively, and FIG. 1d illustrates the needle and suture delivery unit in a needle deploying configuration. The needle and suture delivery unit 100 comprises a needle 140, a pusher 130, and a needle carrier tube 120. The needle 140 and pusher 130 are provided within the needle carrier tube 120 when the needle and suture delivery unit 100 is in a closed configuration, shown in FIG. 1a. A suture 150 is provided with the needle 140. In various embodiments, more than one pusher 130 and needle 140 may be associated with an actuator 201. In the embodiment of FIGS. 1a-1d, four pushers 130 and four needles 140 are provided. Further description of FIGS. 1a-1d is provided below in regard to the suture delivery system. Reference to distal and proximal positions may be made herein. Generally, proximal refers to towards the physician or operator and distal refers to towards the patient. Such reference is for the purposes of illustration only and is not intended to be limiting, and orientations of the various components may be altered.

The handle 200 of the vascular closure delivery system is provided at a proximal end thereof and may be used to control the needle and suture delivery unit 100. First, second, and third actuators 113, 112, and 230 may be provided on the handle 200. The first actuator 113 may be provided on the handle 200 for actuating the legs 110 from a collapsed position to an operational and open position. The second actuator 112 deploys the needle by deploying the actuating members. A third actuator 230 retracts the actuating members after needle deployment.

Figure 2A:
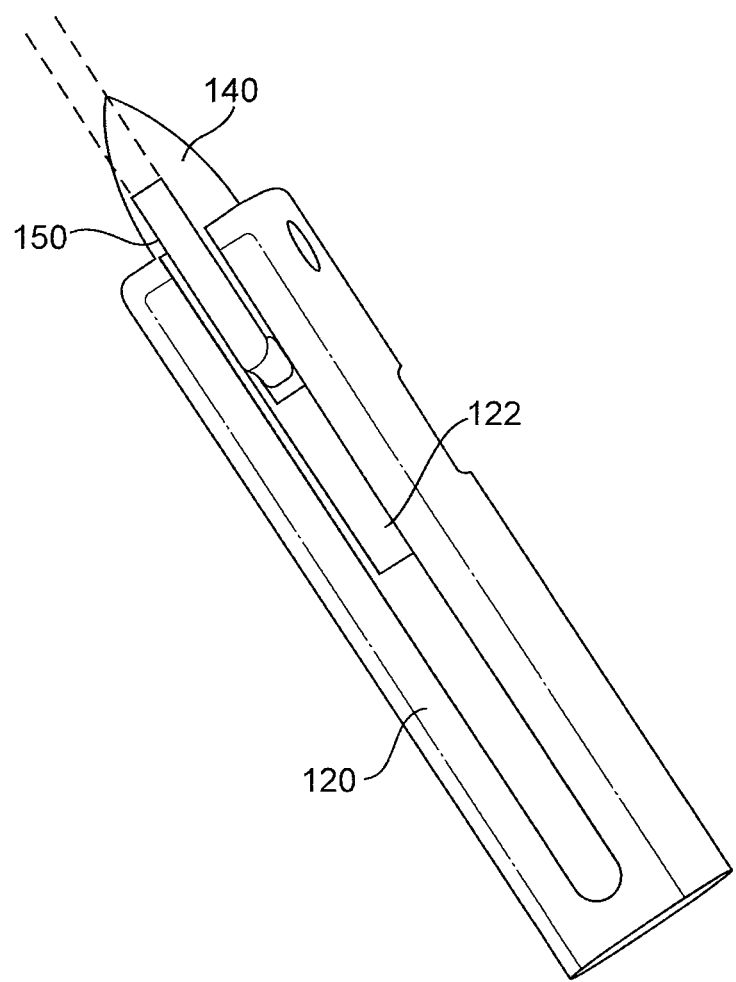
FIG. 2a illustrates a needle having a suture crimped thereto in accordance with one embodiment.
Figure 2B:
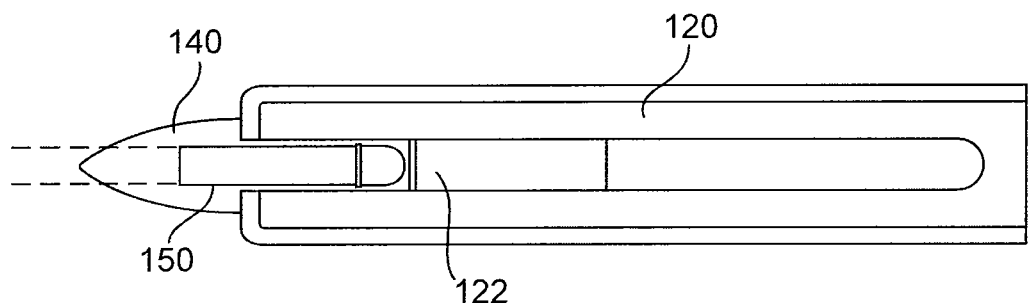

The needle 140 may be constructed of implant grade stainless steel, a dissolvable polymer, a bioresorbable material, or other material suitable for engaging with tissue. The needle 140 includes a sharp end and an opposite end. In one embodiment, the face of the opposite end is approximately perpendicular to a central axis of the needle. In alternative embodiments, the opposite end to the sharp end may have different configurations. The suture 150 may be associated with or coupled to the needle 140 in any suitable manner and at any suitable location. For example, the suture 150 may be threaded through the needle 140, adhered to the needle 140, crimped to the needle 140, injection molded into a needle 140, or other. In one embodiment, shown in FIGS. 2a and 2b, the suture 150 is crimped to the needle 140 generally between the sharp end of the needle 140 and the opposite end of the needle 140. In alternative embodiments, apparatuses other than needles may be provided for placing the suture 150. For example, a pronged projectile or other suitably shaped projectile for engaging with tissue may be provided.

In embodiments where the pusher 130 and needle 140 are provided in a needle carrier tube 120, the pusher 130 expels the needle 140 from the carrier tube 120. Thus, the needle carrier tube 120 has a needle expulsion end from which the needle 140 is expelled to deploy the needle 140 and suture 150. The needle expulsion end may be the distal end of the needle or the proximal end of the needle in various embodiments. In the embodiments shown, the needle expulsion end of the needle carrier tube 120 is the proximal end of the needle carrier tube 120. The pusher 130 likewise has a needle engagement end. The needle engagement end of the pusher 130 is the end of the pusher 130 that engages the needle 140 to expel the needle 140 from the needle carrier tube 120. The pusher 130 may be grounded and/or the needle engagement end of the pusher 130 may have adaptive features to enable coupling with the needle, described more fully below. The needle engagement end of the pusher 130 may be the proximal end of the pusher or the distal end of the pusher in various embodiments. In the embodiments shown, the needle engagement end of the pusher 130 is the proximal end of the pusher 130. Thus, the needle engagement end of the pusher 130 engages the needle 140 to expel the needle 140 from the needle expulsion end of the needle carrier tube 120. More specifically, in the embodiments shown, the proximal end of the pusher 130 engages the needle 140 to expel the needle 140 proximally from the proximal end of the needle carrier tube 120.

In one embodiment, the needle 140 is positioned in the carrier tube 120 such that the sharp end of the needle 140 is oriented toward the needle expulsion end of the carrier tube 120 and the opposite end of the needle 140 is oriented toward the needle engagement end of the pusher 130. In this embodiment, the needle 140 is delivered from the needle carrier tube 120 sharp end-first. Generally, the needle 140 engages with tissue after it is fully delivered from the tube 120. Once the needle 140 engages with tissue, such as by embedding in tissue, it is substantially prevented from re-entering the tube 120.

The pusher 130 may have any suitable configuration for engaging the needle 140. As previously discussed, the needle engagement end of the pusher 130 may have adaptive features to enable the needle engagement end of the pusher 130 to engage the needle 140 or to couple with the needle 140. As shown, the pusher 130 comprises a rod-like structure wherein the needle engagement end of the pusher 130 is configured to be received by the opposite end of the needle 140 such that the needle 140 is carried by the pusher 130. The pusher 130 may be solid or hollow or a combination thereof. In the embodiment shown, the pusher 130 has a generally circular cross section. In other embodiments, the cross section of the pusher 130 may be varied. The pusher 130 is configured and positioned in the needle carrier tube 120 for movement towards an expulsion end of the needle carrier tube 120 to expel the needle 140 therefrom. Such movement is in response to triggering, directly or indirectly, of the actuator 201, described more fully below. The combination of the length of the pusher 130 and the distance the pusher 130 moves may result in the needle engagement end of the pusher 130 moving through and out of the tube 120. In some embodiments, the pusher 130 may exit the tube 120 partially or not at all. The needle engagement end of the pusher 130 may be the distal end of the pusher 130 or the proximal end of the pusher 130.

As shown in FIGS. 1a-1d, the pusher 130 is located at the distal end of the needle and suture delivery unit 100 and pointed towards the proximal end of the needle and suture delivery unit 100 such that the pusher 130 pushes the needle 140 proximally for engagement with tissue. In this embodiment, the needle engagement end of the pusher 130 is the proximal end of the pusher. In alternative embodiments, the pusher 130 may be located at the distal end of the suture assembly or between the proximal end and distal end of the suture assembly with the pusher 130 pointed towards the distal end of the needle and suture delivery unit 100 such that the pusher pushes the needle distally for engagement with tissue. In this embodiment, the needle engagement end of the pusher 130 is the distal end of the pusher 130. Similarly, the expulsion end of the needle carrier tube 120 may be the proximal end of the needle carrier tube 120 or the distal end of the needle carrier tube 120. In the embodiment of FIGS. 1a-1d, the expulsion end of the needle carrier tube 120 is the proximal end.

When a needle 140 is provided at the needle engagement end of the pusher 130, the pusher 130 expels the needle 140 from the tube 120 as the needle engagement end of the pusher 130 moves towards an exit point or expulsion end of the tube 120. After expulsion of the needle 140, the pusher 130 may be retracted back into the tube 120.

Figure 3A:
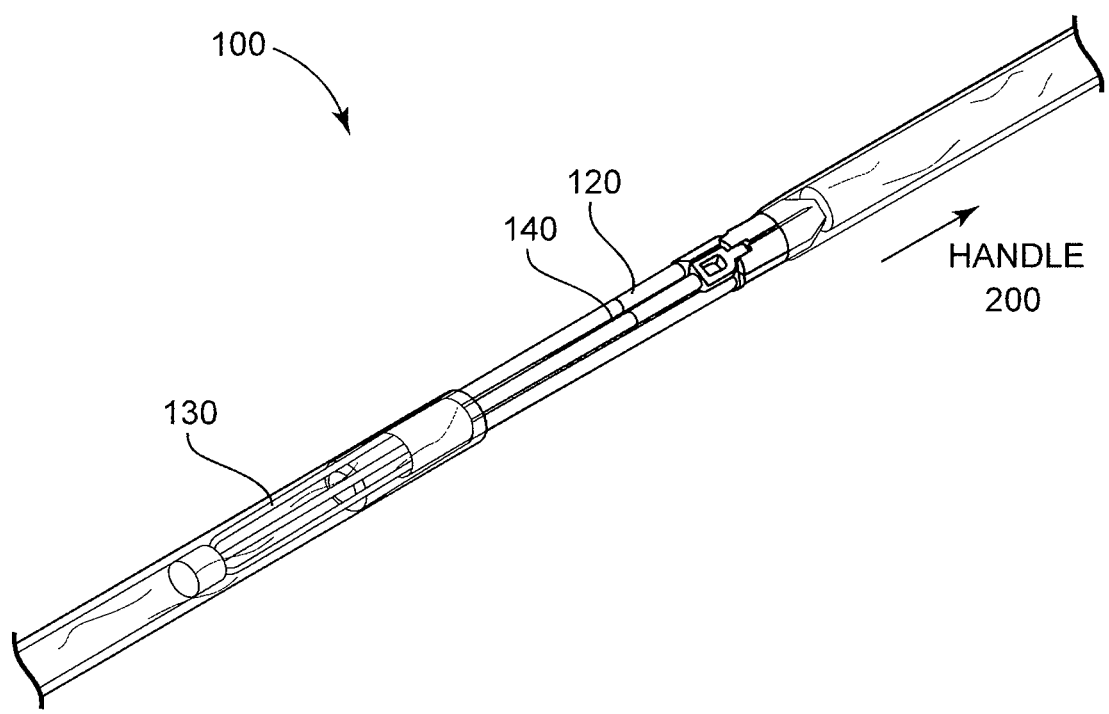
FIG. 3a illustrates a suturing system of the automated needle deployment device, the suturing system in a closed configuration, in accordance with one embodiment.
Figure 3B:
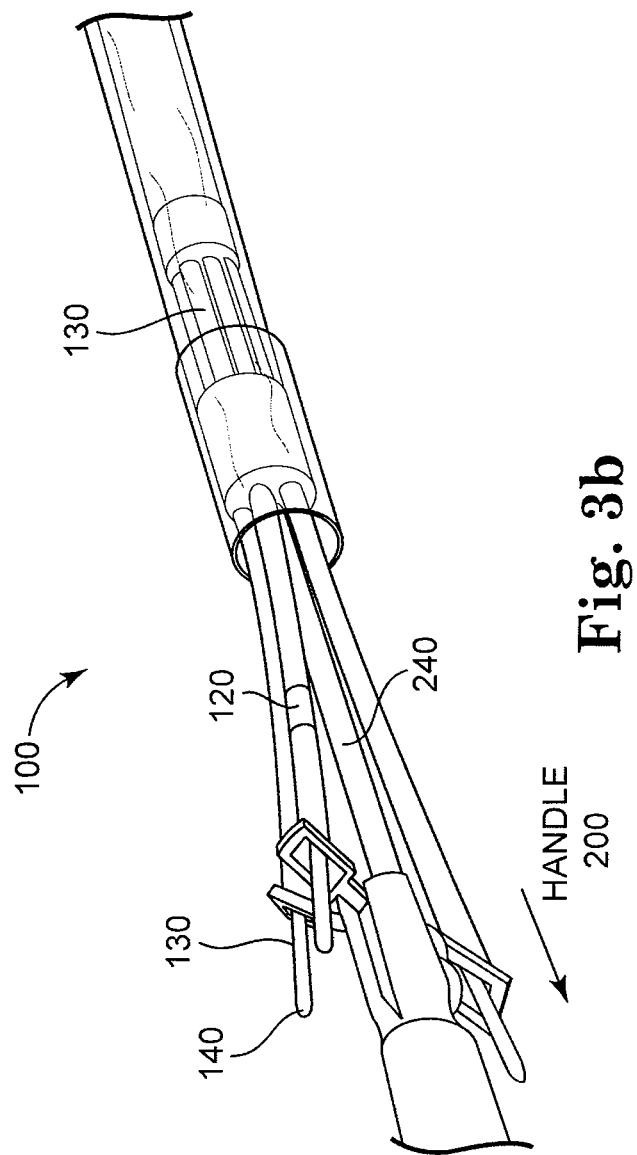
FIG. 3b illustrates a suturing system of the automated needle deployment device, the suturing system in an open configuration, in accordance with one embodiment.

The pusher 130 may be configured to push the needle 140 from the needle carrier tube 120, for example by contacting the opposite end of the needle 140 with the needle engagement end of the pusher 130 and pushing it out of the needle carrier tube 120. Alternatively, as shown in FIG. 3b, the pusher 130 may be configured for carrying the needle 140 out of the needle carrier tube 120. In this embodiment, the cross section of the pusher 130 complements the cross section of the needle 140 and is smaller than the cross section of the needle 140. Further, the opposite end of the needle 140 is at least partially hollow such that it may receive the needle engagement end of the pusher 130. Thus, the needle 140 receives the needle engagement end of pusher 130 at the opposite end of the needle 140. The pusher 130 then may be moved to project from the needle carrier tube 120 and thus carry the needle 140 from the needle carrier tube 120.

Thus, the pusher 130 and needle 140 may be slidably disposed within the needle carrier tube 120 such that the pusher 130 moves therein to expel the needle 140 therefrom, either by pushing the needle 140 from the needle carrier tube 120, by carrying the needle 140 out of the needle carrier tube 120, or other. The needle carrier tube 120 may have any suitable cross section for slidably receiving the pusher 130 and the needle 140. For example, the needle carrier tube 120 may have a circular cross section or a square cross section. In the embodiments shown, the needle carrier tube 120 has a circular cross section. Returning to FIGS. 2a and 2b, the needle carrier tube 120 may have a slot 122 to allow loading of a needle 140 having a suture 150 coupled thereto at between the sharp end of the needle and the opposite end of the needle. In alternative embodiments, for example, where the suture 150 is coupled to the needle 140 at the opposite end thereof, no slot may be provided in the needle carrier tube. The needle 140 within the needle carrier tube 120 may be provided at a needle engagement end of the pusher 130. The needle 140 may be oriented in the tube 120 for expulsion sharp-end first or sharp-end last.

The suture 150 may be composed of a variety of materials such as nylon, a bioresorbable or nonresorbable suture material, metal wire, or any suitable suture material. The suture 150 may be braided. One or more sutures may be associated with each needle 140 or other projectile of the needle and suture delivery unit 100. Thus, at least one end of the suture 150 is associated with a needle 140. Initially, the length of the suture 150 is of a length such that the suture 150 extends from the needle 140 as engaged with the tissue, out of the tissue of the patient, and toward the delivery unit handle. A portion of the suture 150 may be disposed in the tube 120, trailing from the needle 140, before the needle 140 is delivered to tissue.

Movement of the pusher 130 towards the needle expulsion end of the needle carrier tube 120 is triggered by the actuator 201 of the handle 200. The actuator 201 uses a triggered force to automatically deploy the needle 140 via movement of the pusher 130, for example with the push of a button. Such triggered force may be a spring force, a pneumatic force, a magnetic force, or other force. For the purposes of illustration, a spring force is herein described.

As shown in FIGS. 4-7, the actuator 201 comprise a spring 210 and a control 220 The spring is pulled to store energy. Thus, the control 220 keeps the spring 210 in tension until actuation is desired. The control 220 is coupled directly or indirectly to actuating member(s) 240. The actuating member(s) 240 is coupled to the pusher(s) 130. Such coupling may be done in any suitable manner. In one embodiment, the actuating member(s) 240 is crimped to the pusher(s) 130. As shown in FIG. 3b, a single actuating member 240 may be operatively associated with a plurality, for example four, pushers 130. The control 220 is released to cause automated deployment of the needle 140. Such automated deployment is via the actuating members 240 acting on the pusher 130 and the pusher 130 acting on the spring 210. In some embodiments, the control 220 may act on the pusher 130 without an intermediate actuating member. Regardless of whether an actuating member 240 is provided, the pusher 130 is compelled to move towards the expulsion end of the needle carrier tube 120 by release of the spring 210, thus deploying the needle 140 from the needle carrier tube 120. The direction of movement of the pusher 130 may be varied to suit the orientation of the automated needle deployment device. Thus, when it is desired to deploy the needles proximally from a distal position, as shown in FIGS. 1a-1d, the pushers 130 move proximally. This may be done, for example, by exerting a pull force on the pushers 130. Conversely, when it is desired to deploy the needles distally from a proximal position, the pushers move distally. This may be done, for example, by exerting a push force on the pushers 130. Depending on the type of control 220 used, described below, the pusher 130 (and actuating member 240 if provided) may automatically be retracted or may be manually retracted.

Figure 4:
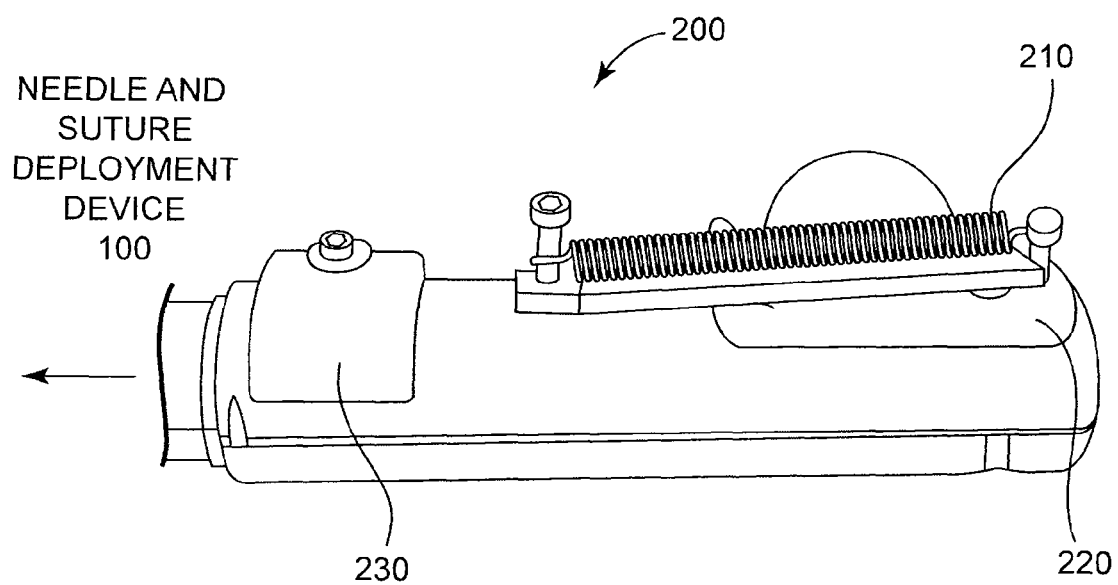
FIGS. 4 illustrates an actuator of the automated needle deployment device, the actuator having a compression spring and the compression spring being in an extended configuration, in accordance with one embodiment.
Figure 5:
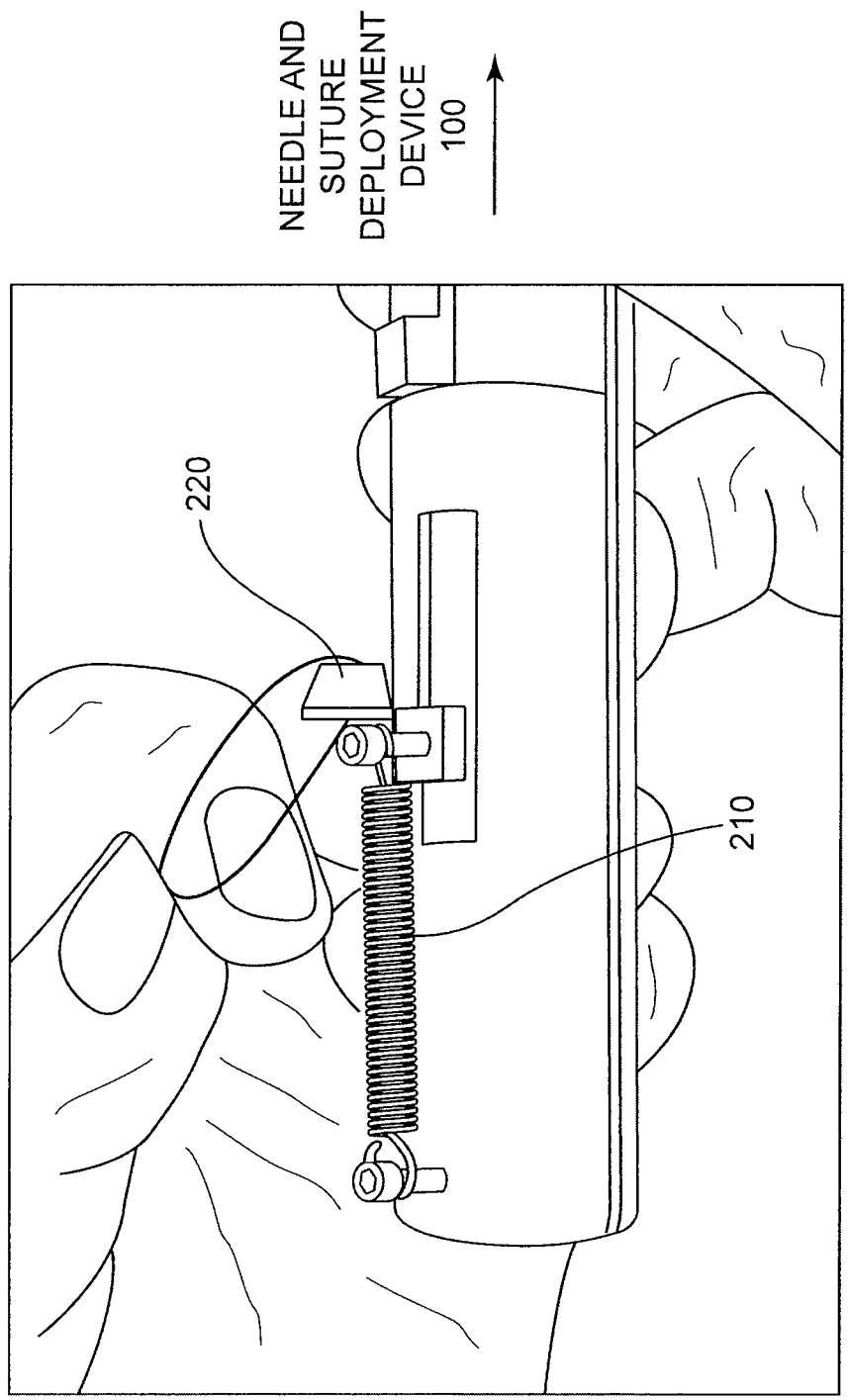
FIG. 5 illustrates the actuator of FIG. 4 with the compression spring in a relaxed configuration.

In one embodiment, shown in FIGS. 4 and 5, the control 220 is a control lever and the spring 210 is a compression spring. As shown in FIG. 4, the compression spring 210 is kept in tension by the lever 220. The control lever 220 is released, for example by pulling of the control lever 220, shown in FIG. 5, to release the spring 210 and move the pusher 130 or actuating member. If an actuating member 240 is provided, the actuating member 240 in turn acts on the pusher 130. The pusher 130 is thus moved (directly by the spring 210 or via the actuating member 240) towards the expulsion end of the needle carrier tube 120 to deploy the needle 140. In one embodiment, an actuating member 240 comprising a nitinol wire is provided. The actuating member 240 has first and second ends. The first end is coupled to the pusher 130 and the second end is coupled to the compression spring 210. When the control lever 220 is released, the spring moves to a released position that moves the extended end of the spring proximally. The proximal movement of the spring causes the actuating member 240 to move proximally, which in turn causes the pusher 130 to move proximally. The proximal movement of the pusher 130 causes the needle 140 to move proximally towards an expulsion end of the tube 120 such that the needle 140 is expelled from the tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130. FIG. 5 illustrates the spring 210 in a released state.

The control lever 220 may be released using any suitable mechanism. For example, a push button or release knob may be provided to release the control lever 220. A second mechanism, shown in FIG. 4 as a push button 230, may be provided to retract that actuating members. A further spring may be provided that is actuated upon pushing of the push button 130, actuation of the spring retracting the actuating member 240. Alternatively, a single mechanism may be provided to release the control lever and retract the actuating members. Such release and retraction may be done using separate actuations of the mechanism.

Figure 6:
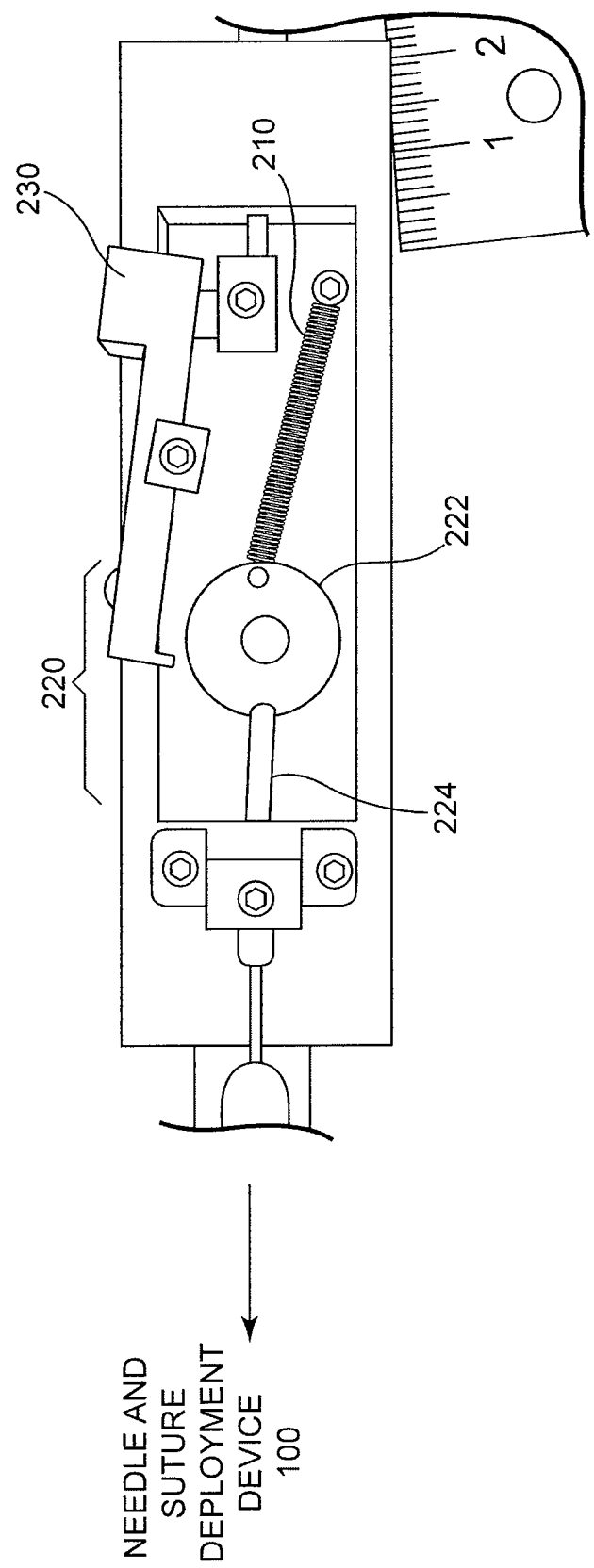
FIG. 6 illustrates an actuator of the automated needle deployment device, the actuator having a flywheel, in accordance with one embodiment.

FIG. 6 illustrates an alternative embodiment using a flywheel control 220 and a compression spring 210. The flywheel control 220 comprises a flywheel 222 and a center rod 224. The center rod 224 is operatively associated with the pusher 130 or, if provided, actuating member. A release button 230 is provided for releasing the compression spring 210, causing the rotation of the flywheel 222. Rotation of the flywheel 222 in turn moves the center rod 224 which causes movement of the actuating member 240 and/or pusher 130. In one embodiment, the center rod 224 is coupled to an actuating member 240 such as a nitinol wire. The actuating member 240 thus is coupled at one end to the pusher 130 and at the other end to the center rod 224. When the flywheel control 220 is released, the flywheel 222 rotates, causing movement of the center rod 224 in the proximal direction. The proximal movement of the center rod 224 causes the actuating member 240 to move proximally, which in turn causes the pusher 130 to move proximally. The proximal movement of the pusher 130 causes the needle 140 to move proximally towards an expulsion end of the tube 120 such that the needle 140 is expelled from the tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130.

With use of a flywheel 222, after movement towards the expulsion end of the needle carrier tube 120, the actuating member 240 and/or pusher 130 automatically retracts into the tube 120 as rotation of the flywheel 222 continues. Thus, half of the revolution of the flywheel drives the or actuating member 240 and/or pusher 130 towards the expulsion end of the needle carrier tube 120 and the other half of the revolution of the flywheel 222 retracts the actuating member 240 and/or pusher 130. Thus, a single mechanism, release button 230, controls release of the spring and retracting of the actuating member 240 and/or pusher 130.

Figure 7:
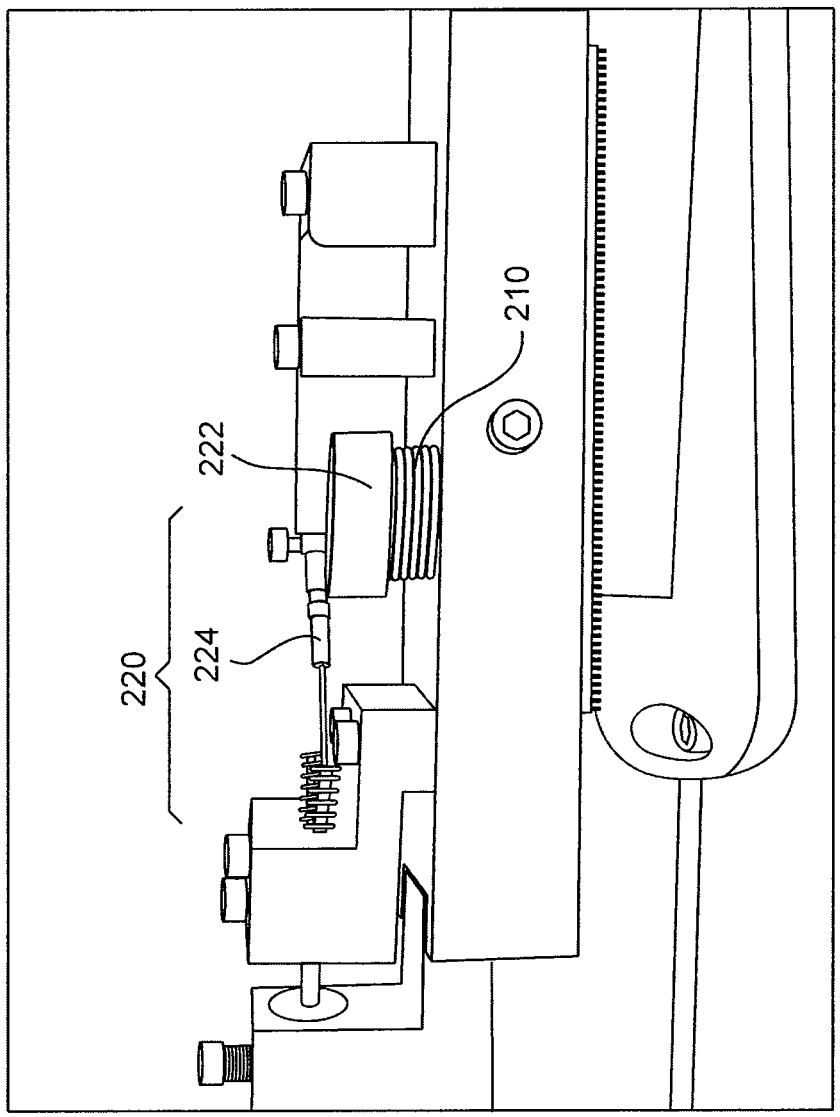
FIG. 7 illustrates an actuator of the automated needle deployment device, the actuator having a torsion spring, in accordance with one embodiment.

An alternative flywheel embodiment is illustrated in FIG. 7 showing a torsion spring. Thus, the control 220 comprises a flywheel 222 and a center rod 224 and the spring 210 comprises a torsion spring. Using a torsion spring, the spring is rotated (rather than pulled) to store energy. A release button 230 is provided for releasing the compression spring 210, causing rotation of the flywheel 222. Rotation of the flywheel 22 in turn moves the center rod 224 which causes movement of the actuating member 240 and/or pusher 130. Rotation of the flywheel 222 in turn moves the center rod 224 which causes movement of the associated pusher 130 or actuating member 240. In one embodiment, the center rod 224 is coupled to an actuating member 240 such as a nitinol wire. The actuating member 240 thus is coupled at one end to the pusher 130 and at the other end to the center rod 224. When the flywheel control 220 is released, the flywheel 222 rotates, causing movement of the center rod 224 in the proximal direction. The proximal movement of the center rod 224 causes the actuating member 240 to move proximally, which in turn causes the pusher 130 to move proximally. The proximal movement of the pusher 130 causes the needle 140 to move proximally towards an expulsion end of the tube 120 such that the needle 140 is expelled from the tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130.

With use of a flywheel 222, after movement towards the expulsion end of the needle carrier tube 120, the actuating member 240 and/or pusher 130 automatically retracts into the tube 120 as rotation of the flywheel 222 continues. Thus, half of the revolution of the flywheel drives the actuating member 240 and/or pusher 130 towards the expulsion end of the needle carrier tube 120 and the other half of the revolution of the flywheel 222 retracts the actuating member 240 and/or pusher 130. Thus, a single mechanism, release button 230, controls release of the spring 210 and retracting of the actuating member 240 and/or pusher 130.

Returning to FIGS. 1*a*-1*d*, suture delivery systems capable of delivering needles and sutures to the tissue are provided. The suture delivery system includes the needle and suture delivery unit 100 and the actuator 201. The actuator 201 may be provided as part of a handle 200 for controlling the needle and suture delivery unit 100. In the embodiment shown, the needle and suture delivery unit 100 includes one or more pushers 130, needles 140, sutures, and legs 110, and is disposed at a distal end of a delivery unit. It is to be noted that, while four sets of legs 110, needle carrier tubes 120, pushers 130, and needles 140 are shown, in alternative embodiments, more or fewer sets of legs, pushers, needle carrier tubes, pushers, and needles may be used. Further, the number of legs, pushers, needles, and sutures may not be equal. The needles 140 and sutures may, more particularly, be delivered to the intima of an artery such as the femoral artery. The needle and suture delivery unit 100 is at least partially insertable into tissue, such as the artery, so that one or more needles and sutures may be delivered to the internal tissue of the patient. A tube or sheath may be provided and may serve as a cover for all or a portion of the needle and suture delivery unit 100. The sheath may be pulled back or peeled away to expose the distal end of the needle and suture delivery unit 100.

FIG. 1*a* illustrates the automated needle deployment device in a closed configuration, FIGS. 1*b* and 1*c* illustrate the automated needle deployment device in a partially open and an open configuration, respectively, and FIG. 1*d* illustrates the automated needle deployment device in a needle deploying configuration. FIG. 1*c* shows the needle and suture delivery unit 100 with the legs 110 in an open position, lifting the needle carrier tubes 120, and FIG. 1*d* shows the needle and suture delivery unit 100 with the pushers 130 and needles 140 extending from the needle carrier tubes 120.

The leg 110 of the needle and suture delivery unit 100 serves as a guide for the tube 120. More specifically, the leg 110 moves the tube 120 from the closed configuration shown in FIG. 1*a* to the open configuration shown in FIG. 1*c* such that the pusher 130 may expel the needle 140 from the tube 120, as shown in FIG. 1*d*. A lever 113 may be provided on the handle 200 for opening the legs. In the embodiment shown, such opening comprises pulling the legs proximally, as described below. The leg 110 may be constructed of stainless steel, a polymer, or any material suitable for medical devices. Reference is made to copending U.S. patent application Ser. No. 11/551,523 filed Oct. 20, 2006; and Ser. No. 11/551,612, filed Oct. 20, 2006, herein incorporated by reference, for specifics regarding actuation of the legs 110. Generally, each leg may be coupled at one end to a support 160 and one or more tensioning cables, and optionally may be coupled at another end to a needle delivery tube 120. The leg 110 is movable from a closed position, shown in FIG. 1a, which is generally parallel to the support 160, to an open position, shown in FIGS. 1b-1c, which is generally perpendicular to the support 160.

In one embodiment, the legs 110 are moved to an open position by deploying a pull force on an actuator 113 disposed on the handle 100. The pull force pulls the needle carrier tubes 120 proximally, thereby pulling the tubes 120 and legs 110 from their collapsed state to an operational and open position. Tactile feedback may indicate to the user to stop applying pull force when the legs 110 have opened. In the open position, the legs 110 are at an angle to the support 160 of approximately 30 degrees to approximately 70 degrees and are flexibly suspended via a tensioning device which may be located at the handle 200.

Figure 8:
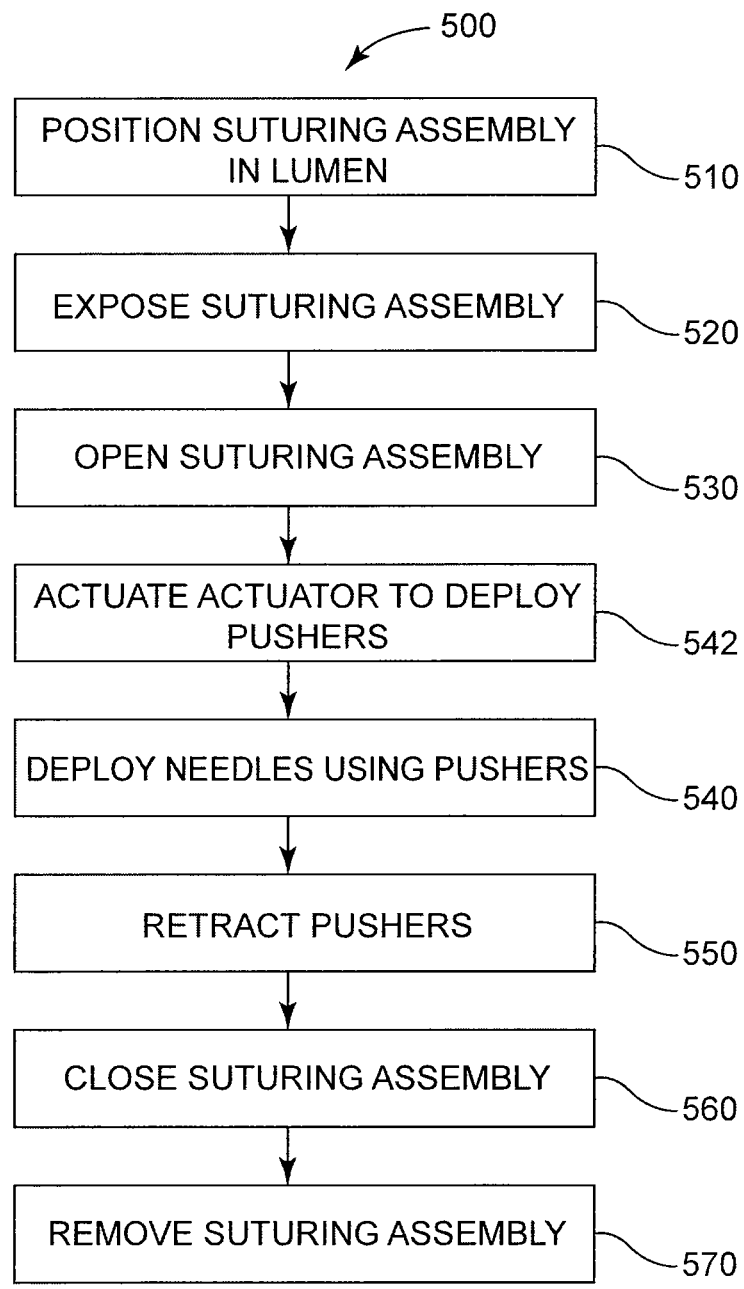
FIG. 8 depicts a method of using the suture system of the present invention.

FIG. 8 depicts one embodiment of a method 500 of using deployment device including the automated needle deployment device. The method 500 involves positioning 510 the suturing system in the lumen for closure of a puncture or wound in the lumen. In one embodiment, positioning 510 the suturing system comprises positioning the needle and suture delivery unit in a lumen using a locator. Using a standard locator, when blood no longer flows through the locator, the correct location has been established. In the embodiment shown in FIGS. 1a-1d the suture deployment device is a "pull-back" device such that the needle and suture delivery unit is positioned in the lumen and pulled back to get tactile feedback. The suturing system may be covered using a sheath. If covered, the needle and suture delivery unit is exposed 520 before deploying the needle and suture. Such exposure may be done by retracting the sheath. If not covered, the needle and suture delivery unit is exposed as positioned. Using a pull back system, tactile feedback further indicates that the legs are positioned proximate the intima of the artery. The needle and suture delivery unit is opened 530 such that the position of components of the needle and suture delivery unit is suitable for needle deployment. In one embodiment, opening 530 comprises opening legs of the needle and suture delivery unit. In some embodiments, the needle and suture delivery unit may be positioned 510 in an open configuration such that no further opening is necessary. The actuator is actuated 542 to deploy the pushers. Such actuating may comprise depressing a push button. The pushers may be deployed directly or via an actuating member. Further, the pushers may be deployed proximally or distally depending on the orientation of the automated needle deployment device. The pushers deploy 540 the needles from the expulsion end of the needle carrier tubes. The expulsion end of the needle carrier tubes may be proximal or distal depending on the orientation of the automated needle deployment device. The pushers are retracted 550. In one embodiment, deployment of the needles is via actuation of a flywheel. The flywheel moves the pushers to deploy the needles. Such movement of the pushers may be via an actuating member. Continued movement of the flywheel causes the pushers to retract. As the pushers retract 550, the needles engage tissue. Engagement of the tissue prevents the needles from retracting with the pushers as the needles toggle and forms a T with the sutures. After the needle and suture delivery unit has deployed the needles, the needle and suture delivery unit may be closed 560, for example by returning the legs to the closed configuration. In some embodiments, it may not be necessary to close the needle and suture delivery unit, for example, where the needles are deployed distally and thus, legs need not have been opened for putting the needle and suture delivery unit in a needle deployment configuration. The needle and suture delivery unit 570 is then removed from the lumen.

Although the present invention has been described with reference to preferred embodiments, persons skilled in the art will recognize that changes may be made in form and detail without departing from the spirit and scope of the invention.

What is claimed is:

1. An automated needle deployment device for insertion of a needle into an internal tissue wall, the automated needle deployment device having a closed position and an open position, having a proximal end proximate to a user and a distal end and comprising:
   a pusher having a needle engaging end;
   a needle, the needle having a sharp end and an opposite end configured for releasably receiving the needle engaging end of the pusher;
   a suture associated with the needle;
   a tube having a needle expulsion end at a proximal end thereof, the tube being, aligned parallel with a longitudinal axis of the automated needle deployment device when in the closed position and arranged at an angle relative to the longitudinal axis when in the open position, wherein the pusher and needle are slidably disposed within the tube, wherein in the closed position and the open position the needle is oriented with the sharp end directed proximally towards the expulsion end of the tube and wherein the pusher is configured to expel the needle from the expulsion end and further to be retracted back into the tube after expelling the needle;
   an actuator operatively associated with the pusher;
   wherein, in the open position, actuation of the actuator moves the pusher towards the needle expulsion end of the tube such that the needle engaging end of the pusher engages the needle and expels the needle proximally from the tube.

2. The automated needle deployment device of claim 1, wherein the needle is concentric with the tube.

3. The automated needle deployment device of claim 1, further comprising an actuating member having first and second ends, wherein the first end of the actuating member is coupled to the pusher and the second end of the actuating member is coupled to the actuator.

4. The automated needle deployment device of claim 1, wherein the actuator comprises a control and a spring and wherein the actuator moves the pusher towards the needle expulsion end by releasing the spring with the control.

5. The automated needle deployment device of claim 4, wherein the control further retracts the pusher.

6. The automated needle deployment device of claim 4, wherein the control is a lever control.

7. The automated needle deployment device of claim 4, wherein the spring is a compression spring.

8. The automated needle deployment device of claim 1, wherein the needle engaging end of the pusher and the opposite end of the needle are complementary such that the opposite end of the needle is received by the needle engaging end of the pusher.

9. The automated needle deployment device of claim 1, wherein the control is a flywheel control.

10. The automated needle deployment device of claim 9, wherein the flywheel control comprises a flywheel and center rod.

11. The automated needle deployment device of claim 1, wherein the spring is a torsion spring.

12. The automated needle deployment device of claim 1, further comprising a mechanism for releasing the actuator.

13. The automated needle deployment device of claim 12, further comprising a second mechanism for retracting the pusher.

14. The automated needle deployment device of claim 1, further comprising an actuating member, the actuator moving the pusher towards the needle expulsion end of the tube via the actuating member.

15. The automated needle deployment device of claim 1, wherein the suture is crimped to the needle between the sharp end of the needle and the opposite end of the needle.

16. The automated needle deployment device of claim 1, wherein the angle is variable to alter a direction in which the needle is expelled from the tube.

* * * * *